United States Patent [19]

Pinkos et al.

[11] Patent Number: 5,382,740
[45] Date of Patent: Jan. 17, 1995

[54] CONTINUOUS PRODUCTION OF CYCLOHEXENE FROM CYCLOHEXYL ESTERS

[75] Inventors: Rolf Pinkos, Bad Durkheim; Rolf Fischer, Heidelberg; Roman Dostalek, Roemerberg, all of Germany

[73] Assignee: BASF Aktiengesellschaft, Ludwigshafen, Germany

[21] Appl. No.: 993,053

[22] Filed: Dec. 18, 1992

[30] Foreign Application Priority Data

Dec. 18, 1991 [DE] Germany .............................. 4141762

[51] Int. Cl.$^6$ ............................................. C07C 1/213
[52] U.S. Cl. ................................... 585/640; 585/638; 585/639
[58] Field of Search ...................... 585/639, 638, 640; 203/29, DIG. 6

[56] References Cited

PUBLICATIONS

Okuhara et al; 'A Pronounced Catalytic Activity of an Acidic Cesium Salt of 12-Tungstophosphonic Acid in Solid-Liquid System' Chem. Letters 1990, pp. 1201-1202.
Adams et al; 'Catalyzed Reactions of Organic Molecules at Clay Surfaces: Ester Breakdown, Dimerization, and Lactonizations'. Jour. Catalysis 78, 197-208, 1982.
Hoben-Weyl, Methoden der organischen Chemie, vol. 5/1b, 1972, p. 105.
Journal of Cat., vol. 78, p. 197 (1982).
Chem. Letters 1990, p. 1201.

*Primary Examiner*—Asok Pal
*Assistant Examiner*—P. Achutamurthy
*Attorney, Agent, or Firm*—Keil & Weinkauf

[57] ABSTRACT

A process for the continuous production of cyclohexene from a cyclohexyl ester of a carboxylic acid having 1 or 2 carbon atoms, which comprises the following steps:
  a) heating a cyclohexyl ester of a carboxylic acid having 1 or 2 carbon atoms in the presence of an acid catalyst with the formation of cyclohexene and a carboxylic acid having 1 or 2 carbon atoms;
  b) removing, by distillation, cyclohexene and carboxylic acid having 1 or 2 carbon atoms from the reaction mixture from stage a) at the same rate as they are formed;
  c) adding a cyclohexyl ester of a carboxylic acid having 1 or 2 carbon atoms to stage a) at the rate cyclohexene and carboxylic acid are distilled off; and
  d) separating the mixture comprising cyclohexene and carboxylic acid having 1 or 2 carbon atoms coming from stage b).

8 Claims, No Drawings

CONTINUOUS PRODUCTION OF CYCLOHEXENE FROM CYCLOHEXYL ESTERS

This invention relates to a process for the production of cyclohexene by breaking down cyclohexyl esters of carboxylic acids having 1 or 2 carbon atoms.

Houben-Weyl, Methoden der organischen Chemie, Vol. 5,/1b, 1972, p. 105 discloses that esters can be broken down by thermolysis in the gas phase at temperatures exceeding 350° C. to form the corresponding carboxylic acid and olefin. Journal of Cat., Vol. 78, p. 197 (1982) discloses that cyclohexyl acetate, dissolved in xylene, dissociates at a temperature of 140° C. in the presence of aluminium montmorillonite to form cyclohexene and acetic acid. Alternatively, Chem. Letters 1990, p. 1201 reveals that cyclohexyl acetate, dissolved in xylene, breaks down in the presence of acid ion exchangers, zeolites in the H form or heteropoly acids, at 100° C. to form cyclohexene and acetic acid. This reference points out that water is injurious to the reaction and the catalysts must therefore be dried before use, since the acidity drops sharply in the presence of water. None of the references reveals what must be done to break down cyclohexyl esters continuously to form cyclohexene and the corresponding acid or how to separate the dissociation products in a simple manner.

It is thus an object of the invention to provide a process for the continuous production of cyclohexene from cyclohexyl esters, which provides high yields and selectivities, and in which water does not lead to a reduction in the activity of the catalysts, and in which simple and efficient separation of cyclohexene and carboxylic acid is effected.

This object is achieved in a process for the continuous production of cyclohexene from a cyclohexyl ester of a carboxylic acid having 1 or 2 carbon atoms, which comprises the following steps:
a) heating a cyclohexyl ester of a carboxylic acid having 1 or 2 carbon atoms in the presence of an acid catalyst with the formation of cyclohexene and a carboxylic acid having 1 or 2 carbon atoms.
b) removing, by distillation, cyclohexene and carboxylic acid having 1 or 2 carbon atoms from the reaction mixture from stage a) at the same rate as they are formed.
c) adding a cyclohexyl ester of a carboxylic acid having 1 or 2 carbon atoms to stage a) at the rate cyclohexene and carboxylic acid are distilled off, and
d) separating the mixture comprising cyclohexene and carboxylic acid having 1 or 2 carbon atoms coming from stage b).

An advantage of our novel process is that it proceeds continuously and is easy to adapt for industrial operation. Another advantage of the novel process is that cyclohexyl esters contaminated with cyclohexanol can be broken down to cyclohexene without previous separation of the cyclohexanol and without any reduction in catalytic activity being ascertainable. Another advantage of the novel process is that the separation of cyclohexene and carboxylic acid takes place in a simple manner.

The starting point for the process comprises cyclohexyl esters of carboxylic acids having 1 or 2 carbon atoms. These comprise cyclohexyl formate and cyclohexyl acetate and mixtures thereof. Furthermore, the cyclohexyl esters used as starting material can contain up to 30 wt % of cyclohexanol. Such mixtures of cyclohexyl acetate or formate with cyclohexanol are formed, e.g., during separation of cyclohexene from mixtures produced in the partial hydrogenation of benzene.

In the first stage—stage a)—there are heated cyclohexyl esters of carboxylic acids having 1 or 2 carbon atoms in the presence of acid catalysts, with the formation of cyclohexene and carboxylic acids having 1 or 2 carbon atoms.

The acid catalysts used are advantageously zeolites in the H form, acid ion exchangers, heteropoly acids, and also acidic and hyperacidic metal oxides.

It is preferred to use zeolites in the mordenite group or fine-pored zeolites of the erionite species, chabazite species, or zeolites of the faujasite species, e.g., zeolites of type X, Y, or L. This group also includes the so-called ultrastable zeolites of the faujasite species, i.e., dealuminated zeolites. Particularly favorable representatives of the zeolites are those having pentasile structure, such as ZSM 5, ZSM 11 and ZMB 10. These have in common, as main building block, a five-membered ring composed of $SiO_2$-tetrahedra. They are characterized by a high $SiO_2/Al_2O_3$ ratio and by pore sizes which lie between those of the zeolites of species A and those of the species X or Y.

Other acid catalysts advantageously used are inorganic heteropoly acids which possess at least two different center atoms. The following are examples thereof: dodecatungstatophosphoric acid and dodecamolybdatophosphoric acid. Preferred heteropoly acids are heteropoly acids of molybdenum or tungsten with phosphoric acid, telluric acid, selenic acid, arsenic acid, or silicic acid, preferably with phosphoric acid. Some of the protons of the heteropoly acids can be replaced by metal ions, preference being given to alkali metal ions and alkaline-earth metal ions.

Also suitable, as acid catalysts, are acid ion exchangers, e.g., cross-linked polystyrenes containing sulfonic acid groups.

Other suitable acid catalysts are acid metal oxides, such as silicon dioxide, aluminum oxide, zirconium dioxide, titanium dioxide, and tin dioxide, which can be treated if desired, for reinforcement, with a mineral acid such as sulfuric acid.

Other suitable catalysts are mineral acids, such as sulfuric acid or phosphoric acid, and also organic acids, such as sulfonic acids, e.g., benzenesulfonic or toluenesulfonic acid.

It is advantageous to use from 5 to 700 kg and preferably from 50 to 400 kg of cyclohexyl esters of carboxylic acids having 1 or 2 carbon atoms per kilogram of catalyst per hour, optionally together with cyclohexanol.

It has proven advantageous to keep to residence times ranging from 1 min to 180 min and preferably of from 3 to 90 min and more preferably of from 5 min to 60 min. Advantageously, a temperature of from 50° to 200° C. and preferably of from 70° to 180° C. and more preferably of from 90° to 150° C. is used. Good results are obtained when the temperature is chosen such that the dissociation products can distill off easily. It is possible to carry out the reaction under standard pressure or slightly elevated pressure or slightly reduced pressure, e.g., a pressure of from 0.1 to 10 bar and preferably from 0.3 to 5 bar and more preferably from 0.8 to 2 bar.

In step b), cyclohexene and carboxylic acid, i.e., acetic acid or formic acid, are distilled off from the reaction mixture at the same rate as they are formed.

The reaction mixture essentially consists of the aforementioned esters of cyclohexanol, a small amount of cyclohexanol, and the catalyst used, as well as the dissociation products cyclohexene and acetic acid or formic acid, and possibly some water.

Step c) comprises passing to stage a) cyclohexyl esters of carboxylic acid having 1 or 2 carbon atoms, optionally together with cyclohexanol, at the same rate as cyclohexene and carboxylic acid are distilled off.

In step d) cyclohexene and carboxylic acid having 1 or 2 carbon atoms coming from step b), are separated, e.g., by distillation or phase separation.

If cyclohexyl acetate is used as starting material, it is advantageous to separate the distillate mixture of cyclohexene and acetic acid, optionally together with water, in a column. Cyclohexene distills off at the head of the column as pure substance, whilst acetic acid is withdrawn, possibly together with water, as a sidestream at a point down the column.

In a preferred embodiment, the vapors produced in step b) and consisting of cyclohexene, formic acid or acetic acid, and possibly water, are condensed and caused to separate, if necessary by adding water, into a phase substantially consisting of cyclohexene and a phase substantially consisting of water and formic acid or acetic acid. The cyclohexene phase is distilled to give pure cyclohexene, whilst the possibly aqueous carboxylic acid can be reused, e.g., for the separation of cyclohexene from the benzene hydrogenation, mixture.

Cyclohexene, such as is produced by the process of the invention, is suitable, e.g., for the preparation of cyclohexene oxide.

The process of the invention is illustrated below with reference to the following examples.

Example 1

In a reaction vessel having a capacity of 100 mL there were placed 1 g of $H_{0.5}Cs_{2.5}PW_{12}O_{40} \cdot xH_2O$ and 50 mL of cyclohexyl formate. The charge was heated at 115° C. with stirring under a blanket of nitrogen, and the reaction product was distilled off through a column. The quantity of distillate was continuously made good by passing in fresh cyclohexyl formate to the reaction vessel. The temperature of the distillate at the top of the column was 73° C. (1013 mbar). The distillate separated in a receiver into two phases. In this way, a total of 970 g of cyclohexyl formate was reacted over a period of 8 hours. The residence time was ca 0.5 h. When the reaction was stopped, it was not possible to detect any deactivation of the catalyst. The phases in the reactor output were separated portionwise and analyzed to determine their composition.

The following composition was found for the top phase:

The content of cyclohexene, by weight, fluctuated between 95 and 98%, and that of formic acid ranged from 2 to 4%. The residue (not more than 1%) comprised cyclohexyl formate.

The bottom phase was found to have the following composition:

The content of cyclohexene, by weight, varied between 1 and 2%, and the content of formic acid, by weight, ranged from 98 to 99%. Small contents (less than 0.5%) of cyclohexyl formate were also found.

The bottoms contained, in addition to cyclohexyl formate, cyclohexene, and formic acid, small amounts of cyclohexylcyclohexene and traces of cyclohexylcyclohexanol. These by-products were, however, already present in the cyclohexyl formate used.

The selectivity toward cyclohexene and formic acid was better than 99%, based on cyclohexyl formate used.

Example 2

Using a procedure analogous to that employed in Example 1 there were reacted 500 g of cyclohexyl acetate with 1 g of tungstophosphoric acid. When operating with residence times of from 0.4 to 0.6 h and at a bottom temperature of from 121° to 125° C. and a top temperature of from 87° to 98° C., a single-phase effluent was obtained. This exhibited a content of cyclohexene, by weight, of from 55 to 65% and a content of acetic acid, by weight, of from 35 to 45%. There were occasionally found small amounts of cyclohexyl acetate (less than 0.5%). The selectivities toward cyclohexene and acetic acid, based on cyclohexyl acetate used, were better than 99%.

100 g of the combined reactor outputs were mixed with 1.6 g of water. Immediate phase separation occurred, and 80% of acetic acid, by weight, was found to be present in the bottom phase (ca 20 g).

Example 3

Using a procedure analogous to that employed in Example 1 there were reacted 277 g of a mixture of 80 mol % of cyclohexyl acetate and 20 mol % of cyclohexanol with 1 g of tungstophosphoric acid. When operating with residence times of 0.6 h there were obtained, at bottom temperatures of 125° C. and top temperatures of ca 96° C., two-phase effluents of the following composition:

The top phase exhibited average contents of cyclohexene, by weight, of 82% and average contents of acetic acid, by weight, of 17%. The residues consisted of cyclohexyl acetate and water.

The bottom phase exhibited contents of cyclohexene, by weight, of from 4 to 10%, and contents of acetic acid, by weight, of from 80 to 85%. In all cases, the residue consisted of water and small amounts of cyclohexyl acetate.

The selectivity toward cyclohexene and formic acid was better than 99%, based on the cyclohexyl acetate/cyclohexanol used.

We claim:

1. A process for the continuous production of cyclohexene from a cyclohexyl ester of a carboxylic acid having 1 or 2 carbon atoms, which comprises the following steps:

a) heating a cyclohexyl ester of a carboxylic acid having 1 or 2 carbon atoms in the absence of a solvent for said ester but in the presence of an acid catalyst with the formation of cyclohexene and a carboxylic acid having 1 or 2 carbon atoms;

b) removing, by distillation, cyclohexene and carboxylic acid having 1 or 2 carbon atoms from the reaction mixture from stage a) at the same rate as they are formed;

c) adding a cyclohexyl ester of a carboxylic acid having 1 or 2 carbon atoms to stage a) at the rate cyclohexene and carboxylic acid are distilled off; and d) separating the mixture comprising cyclohexene and carboxylic acid having 1 or 2 carbon atoms coming from stage b).

2. The process of claim 1, wherein the acid catalyst used is a zeolite, an acid ion exchanger, a heteropoly acid, or an acidic or hyperacidic metal oxide.

3. The process of claim 1, wherein from 5 to 700 kg of cyclohexylester of a carboxylic acid having 1 or 2 carbon atoms are used per kilogram of catalyst per hour.

4. The process of claim 1, wherein the temperature in stage a) is kept between 90° and 150° C.

5. The process of claim 1, wherein the residence time in stage a) is adjusted to from 3 minutes to 90 minutes.

6. The process of claim 1, wherein cyclohexene and carboxylic acid coming from stage b) are condensed, water is added to the condensate, and a phase essentially comprising cyclohexene is separated from a phase essentially comprising water and carboxylic acid having 1 or 2 carbon atoms.

7. The process of claim 1, wherein in step a), the cyclohexyl ester is heated along with cyclohexanol.

8. The process of claim 1, wherein the mixture from stage d) is separated in a column, cyclohexene being taken off as an overhead product, and acetic acid being withdrawn as a side stream at a point down the column.

* * * * *